US009295374B2

(12) United States Patent
Metras

(10) Patent No.: US 9,295,374 B2
(45) Date of Patent: Mar. 29, 2016

(54) PRESSURE COMPENSATION CAP FOR ENDOSCOPES

(71) Applicant: Karl Storz Endovision, Inc., Charlton, MA (US)

(72) Inventor: Stephen Metras, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 56 days.

(21) Appl. No.: 13/644,608

(22) Filed: Oct. 4, 2012

(65) Prior Publication Data

US 2014/0100425 A1    Apr. 10, 2014

(51) Int. Cl.
*A61B 1/12*    (2006.01)
*A61B 1/00*    (2006.01)

(52) U.S. Cl.
CPC ............... *A61B 1/00137* (2013.01); *A61B 1/12* (2013.01); *A61B 1/121* (2013.01)

(58) Field of Classification Search
CPC .......... A61B 1/00121; A61B 1/00137; A61B 1/00119
USPC ............... 600/121, 133, 158, 159; 604/99.02, 604/99.03, 99.04, 167.03, 167.04, 167.05
See application file for complete search history.

(56) References Cited

U.S. PATENT DOCUMENTS

| 4,878,484 | A |   | 11/1989 | Miyagi |   |
|---|---|---|---|---|---|
| 5,547,456 | A |   | 8/1996 | Strobl et al. |   |
| 5,807,238 | A |   | 9/1998 | Feldman et al. |   |
| 5,868,667 | A |   | 2/1999 | Lin et al. |   |
| 6,053,861 | A | * | 4/2000 | Grossi | 600/154 |
| 7,998,057 | B2 | * | 8/2011 | Kain | 600/38 |
| 2004/0096355 | A1 | * | 5/2004 | Ishibiki | 422/26 |

OTHER PUBLICATIONS

European Search Report Application No. EP 13 18 6593 Completed: Jan. 14, 2014; Mailing Date: Jan. 22, 2014 5 pages.

* cited by examiner

*Primary Examiner* — Anhtuan T Nguyen
*Assistant Examiner* — Timothy J Neal
(74) *Attorney, Agent, or Firm* — Whitmyer IP Group LLC

(57) ABSTRACT

A pressure compensation cap, system, and method for equalizing pressure in an endoscope while preventing a liquid from entering an interior of the endoscope through an opening. The cap is adapted to fit over an opening in the endoscope and includes a hole occluded by a filter. The filter is made with a material which allows certain gasses to pass through the cap into or out of the endoscope while preventing certain liquids from passing through at certain pressures and temperatures. The liquids, gasses, pressures, and temperatures may include those typically encountered when sterilizing an endoscope, those typically encountered during transport of an endoscope by air or otherwise, or those encountered at any time during the lifecycle of an endoscope.

26 Claims, 5 Drawing Sheets

PRESSURE COMPENSATION CAP FOR ENDOSCOPES

FIELD OF THE INVENTION

The present invention relates to pressure compensation devices, and in particular relates to a pressure compensation cap for an endoscope which allows air or other gasses to pass but which prevents or substantially impedes water or other liquids from passing.

BACKGROUND OF THE INVENTION

A typical endoscope features an elongated tube suitable for introduction into a human or animal body. A lens at a distal tip of the endoscope forms an image of an internal area of the body. Fiber optic cables, wires, or lenses may occupy tubular passages which run the length of the endoscope in order to transmit the image from the internal area of the body at the distal end to an eyepiece or image capturing device at the proximal end.

Gasses, liquids, instruments, or control cables may also pass through passages between the distal and proximal ends. A sheath or other surface usually covers the exterior of the endoscope in order to protect the body from the internal parts of the endoscope, and to protect the endoscope from the environment of the body. Typically the endoscope is air- and water-tight except for the openings of the tubular passages, which may have caps, covers, or valves for sealing the openings when the endoscope is not in use.

Endoscopes are typically washed and sterilized before and after use in medical applications. Endoscopes may be washed by immersion in a liquid such as water or a cleaning fluid, and may be sterilized by immersion in a sterilization fluid or by exposure to a sterilizing gas, which may take place in a reduced pressure environment.

However a typical endoscope having an air- and water-tight structure when capped can be damaged by pressure differentials arising between the interior and the exterior of the endoscope during sterilization. Endoscopes are also routinely transported via air during shipping which can also result in pressure differentials.

In order to address this problem, pressure compensation caps may be provided for covering endoscope openings under these circumstances. Where an air- or water-tight cap or valve would prevent relief of pressure differentials during shipping or sterilization, a compensation cap is configured to equalize the pressure. Pressure compensation caps may have openings which allow liquids and gasses to pass through, and may incorporate valves and/or valve actuators which hold open valves that are integral or assembled with the endoscope.

Typically, pressure compensation caps are designed only for use during storage and shipping of endoscopes, for dry sterilization processing where the endoscope is exposed to a high vacuum, and for gas sterilization where the endoscope is exposed to a sterilizing gas such as ethylene oxide ("ETO"). Separate water resistant caps for endoscopes are available for use with a wet sterilization process.

Routinely however, endoscopes are returned to the manufacturer for evaluation and repair due to fluid ingress. It is suspected that this fluid ingress is due to the end user sterilizing the endoscope using a wet process while leaving the pressure compensation cap in place. This results in needless returns of endoscopes for evaluation and repair.

Water resistant caps often closely resemble a pressure compensation cap. This means that not only are multiple caps required for different sterilization processes and transport, but there is a chance that an end user will mistake one cap for the other, resulting in damage to the endoscope. This damage may be caused either by the fluid ingress described above if a pressure equalization cap is used in a wet sterilization process, or rupture or other damage to the components of the endoscope if a water resistant cap is used in a vacuum sterilization process due to the resulting pressure differential.

It is therefore desired to provide a pressure compensation cap which addresses these deficiencies.

SUMMARY OF THE INVENTION

Accordingly, it is an object of the present invention to provide a pressure compensation cap for an endoscope which enables pressure equalization while preventing fluid ingress.

It is another object of the present invention to provide a pressure compensation cap for an endoscope which can remain in place on an endoscope during a wet sterilization process.

It is a further object of the present invention to provide a water resistant cap for an endoscope which also enables pressure equalization between the interior and exterior of an endoscope.

It is yet another object of the present invention to provide a cap for an endoscope which equalizes pressure between an interior and an exterior of an endoscope when the interior pressure is greater than the exterior pressure, and also prevents fluid ingress.

It is still a further object of the present invention to provide a cap for an endoscope which equalizes pressure between an interior and an exterior of an endoscope when the interior pressure is less than the exterior pressure, and also prevents fluid ingress.

It is yet a further object of the present invention to substantially prevent the ingress of typically encountered fluids into an interior of an endoscope while allowing typically encountered gasses to pass between the interior and exterior of the endoscope at typically encountered pressures.

These and other objects are achieved by providing a system for equalizing pressure in an endoscope while preventing a liquid from entering an interior of the endoscope through an opening in the endoscope which includes an endoscope having an opening; a cap fitting over the opening; a hole in the cap; and, a filter occluding the hole and made from a material which permits a gas to pass through the filter and which prevents the liquid from passing through the filter.

In some implementations, the filter includes a material having a surface energy lower than the surface energy of the liquid. The filter may additionally or alternatively include a porous material having a pore size which permits the gas to pass through the cap while preventing the liquid from passing through the cap, and may be made from a material including porous PTFE.

In some implementations, the liquid includes water. The liquid may additionally or alternatively include a sterilization fluid, and may include at least one substance selected from the group consisting of sodium hypochlorite, glutaraldehyde; formaldehyde; ortho-phthalaldehyde; hydrogen peroxide; and peracetic acid.

In some implementations the gas comprises air. The gas may additionally or alternatively include at least one substance selected from the group consisting of ethylene oxide; ozone; hydrogen peroxide; and chlorine.

Other objects of the invention are achieved by providing a cap for equalizing pressure in an endoscope which is adapted to fit over an opening in the endoscope and which includes a filter made from a material which permits a gas to pass through the cap while preventing a liquid from passing through the cap.

Further objects of the invention are achieved by providing a method of equalizing pressure in an endoscope while excluding a liquid from an interior of the endoscope, comprising the steps of providing a cap having a hole; occluding the hole with a filter made from a material which permits gasses to pass through the filter while preventing liquids from passing through the filter; and, fitting the cap over an opening in the endoscope.

These and other objects of the invention and its particular features and advantages will become more apparent from consideration of the following drawings and accompanying detailed description.

DETAILED DESCRIPTION OF THE INVENTION

Figure 1:
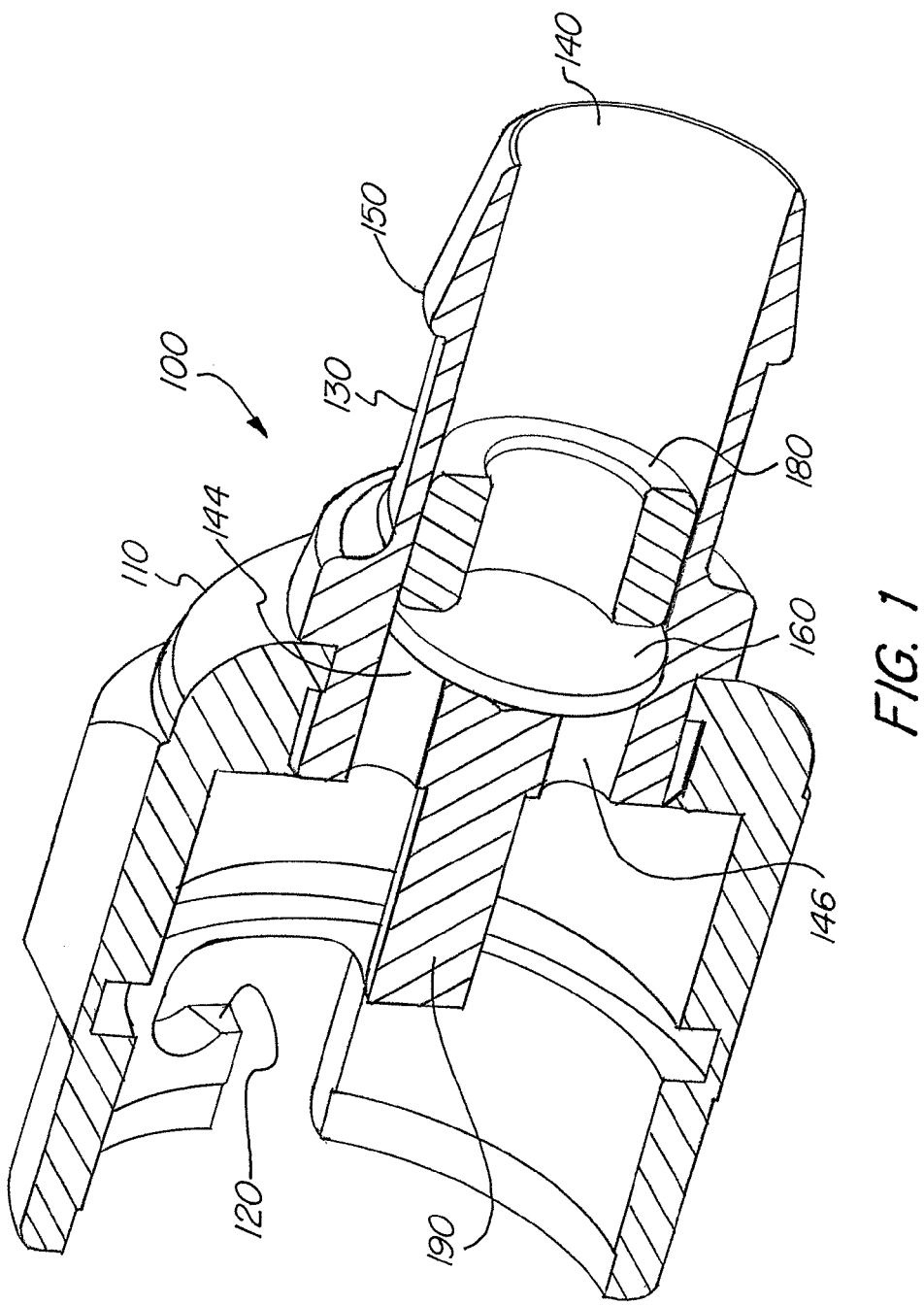
FIG. 1 is a perspective cross-sectional view of an example pressure compensation cap which illustrates aspects of the invention.

FIG. 1 is a perspective cross-sectional view of an example pressure compensation cap 100 which illustrates aspects of the invention.

Figure 6:
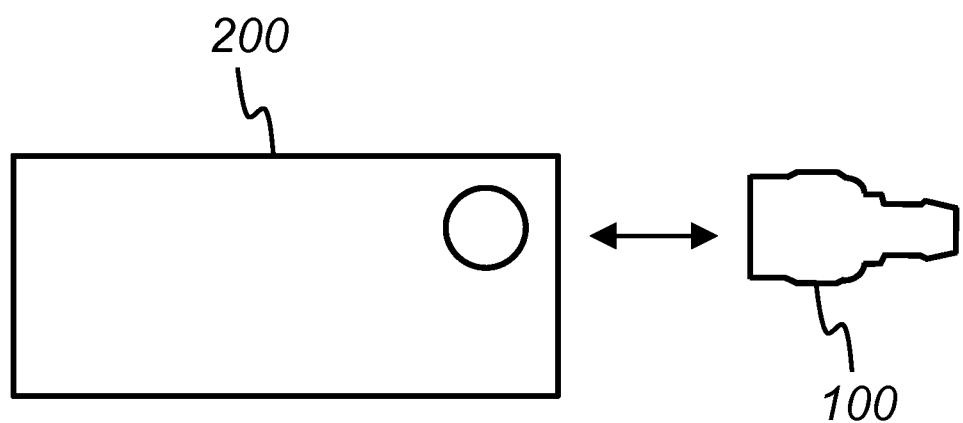
FIG. 6 is side view of the pressure compensation cap illustrated in FIG. 1 to be fitted in an opening of an endoscope.

Cap 100 includes a cap body 110 which may be fitted to an opening of an endoscope 200 using a suitable connector (see FIG. 6). In this example application, cap body 110 employs a bayonet style connector 120, however, it is envisaged that another suitable connecting mechanism known in the art may also be used.

Cap 100 also includes insert 130. Insert 130 is fitted to cap body 110, and has a channel 140. Insert 130 may be fitted to cap body 110 as shown in FIG. 1, or may be attached using a screw fitting, press fitting, or another suitable fitting known in the art (not shown). Insert 130 may incorporate a fitting 150 for connecting insert 130 to another element, such as a hose for supplying gas or vacuum (not shown). In this example application, fitting 150 is a hose barb fitting, however, it is envisaged that another suitable connecting mechanism known in the art may also be used.

Cap insert 130 may optionally be constructed in one piece with cap 100 without departing from the invention.

When cap 100 is fitted to an endoscope, the joint between cap body 110 and the endoscope (not shown) as well as the joint between cap body 110 and insert 130 are intended to be substantially liquid-tight when exposed to liquids and pressures encountered in typical applications as understood by those having skill in the art.

Channel 140 is divided at one end into sub-channels 144 and 146. It will be understood by those having skill in the art that channel 140 may, in some implementations, continue undivided along its entire length, or may include multiple channels or branches without departing from the invention.

Dividing channel 140 into sub channels in this way can have the advantage of enabling an optional seat 170 or optional stem 190 to be incorporated into the cap insert 130 or otherwise into cap 100.

Optionally, a stem 190 is provided, which may be integral with the insert 130. Stem 190 may be adapted to actuate and/or hold open a valve of an endoscope when cap 100 is fitted to an opening of the endoscope (not shown). Stem 190 may be positioned such that it does not obstruct sub-channels 144 and 146.

Filter 160 is disposed within channel 140 and completely occludes channel 140, as well as sub-channels 144 and 146.

Filter 160 is made from a material which prevents liquids from passing through it, yet permits gasses to pass through it, when exposed to liquids and pressures encountered in typical applications. In an example application, valve element 160 would prevent water from passing through, but would permit air or ETO gas to pass through.

Filter 160 is made from or may include a material having a property which provides the function of allowing gasses to pass while blocking liquids. This function may be provided by one or more properties of the material, including a pore size, thickness, surface area, and/or surface energy, and may be affected by or depend upon the pressure differential between an interior and exterior of the endoscope or the pressures of the liquids and/or gases (not shown).

Filter 160 may be shaped such that its geometry facilitates its function as a liquid impermeable gas permeable boundary. For example, Filter 160 may be of a thickness sufficient to provide this property for a given material. Filter 160 may also have a shape which facilitates its seating within insert 130 such that it maintains its occlusion of channel 140, and/or resists the pressure of flowing liquids or gasses.

Filter 160 may also be constructed as a cartridge containing an arrangement of membranes (not shown).

Filter 160 may be made with an expanded polytetraflouroethelyne ("PTFE") membrane, sintered PTFE, another fluoroplastic, polysulfone, polymer, monomer, ceramic, composite, equivalent porous membrane, porous solid, or porous composite, or another material or combination of materials known in the art which can provide the necessary functionality. The material of filter 160 may have a dimension or dimensions such as pore size, depth, volume, width, length, and/or surface energy which alone or in combination prevents typically encountered liquids from passing through filter 160 at pressures typically encountered during use. In some applications, the surface energy of the filter material may be lower than such liquids. In some applications, filter 160 may not prevent passage of certain liquids at certain pressures, so long as typically encountered or specified liquids are blocked at typically encountered or specified pressures.

A seat 170 may be disposed within channel 140 and may be configured to support filter 160. Seat 170 may be disposed in insert 130, disposed in stem 190, or may be a surface or surfaces of insert 130 and/or stem 190. In other implementations, filter 160 can be seated within cap 100 in another way which prevents the passage of liquids without departing from the invention (not shown).

Retainer 180 is disposed within channel 140 and maintains the seating of filter 160 in seat 170. In this example application, retainer 180 is configured as a retaining ring which is press-fit within channel 140 such that filter 160 is held within seat 170. Retainer 180 is configured such that it does not completely occlude channel 140 or subchannels 144 and 146.

Figure 2:
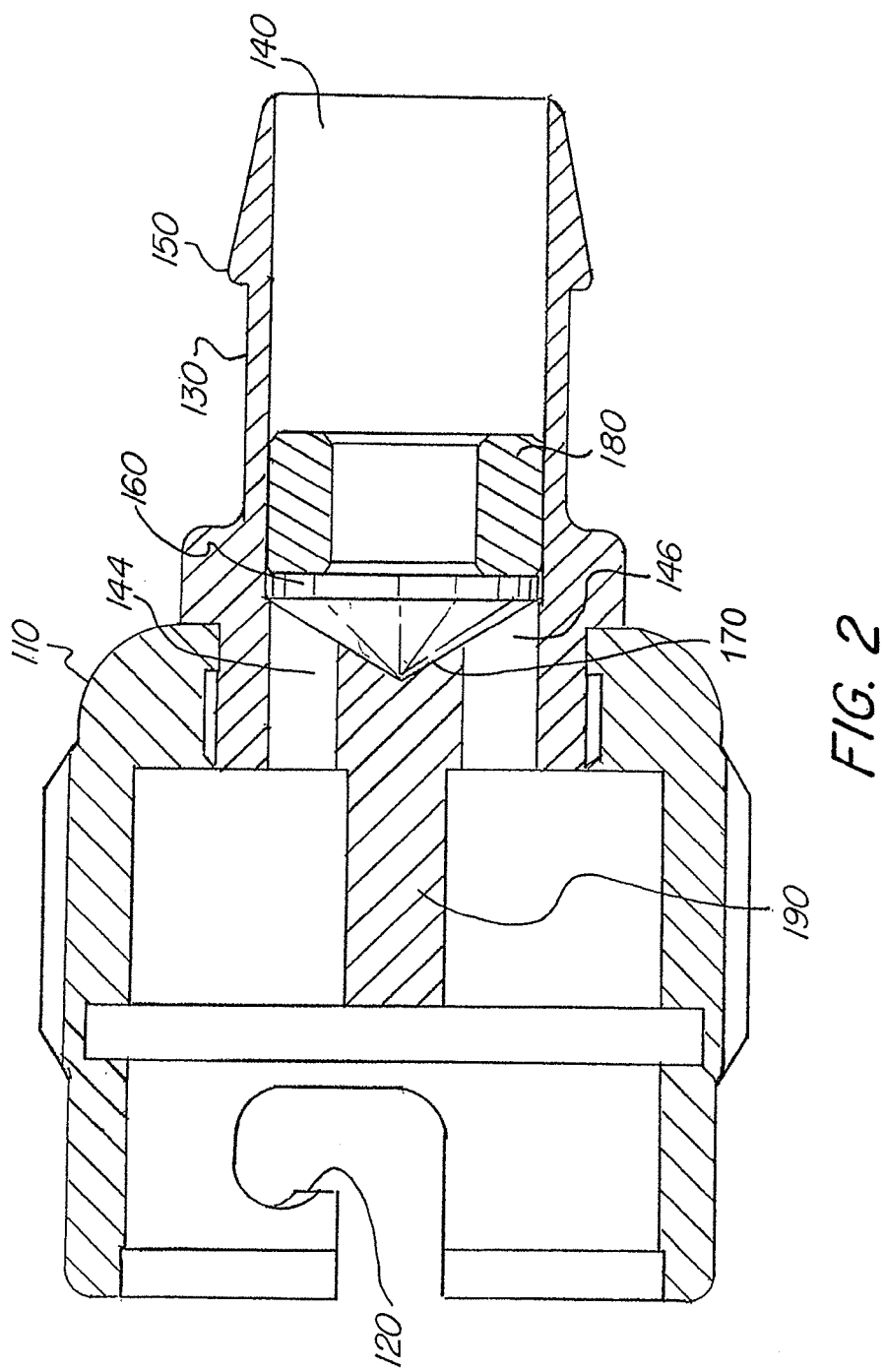
FIG. 2 is a side cross-sectional view the pressure compensation cap illustrated in FIG. 1.

FIG. 2 is a side cross-sectional view of cap 100.

Figure 3:
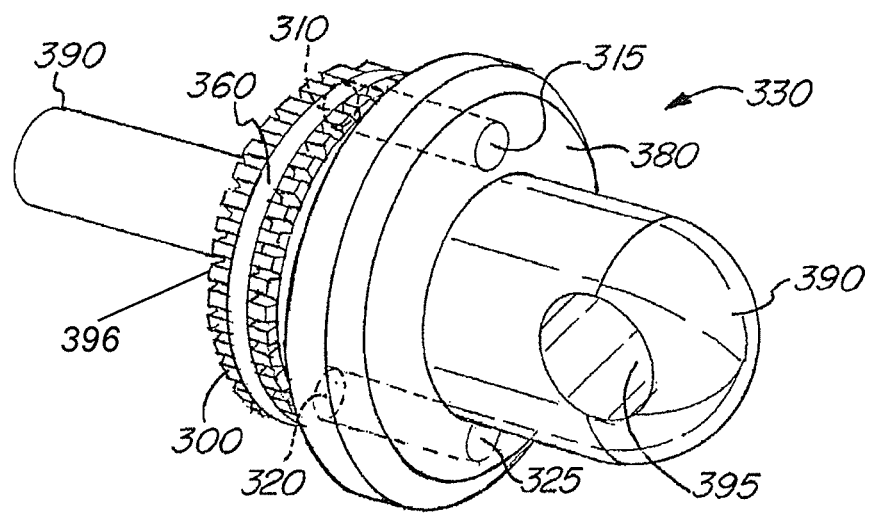
FIG. 3 is a perspective view of an example insert which illustrates aspects of the invention and which may be used with the cap illustrated in FIGS. 1 and 2.
Figure 4:
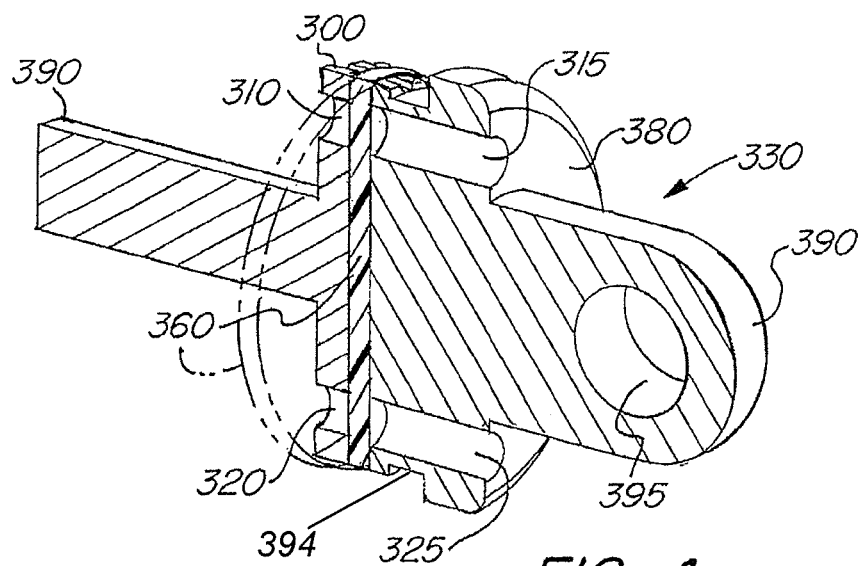
FIG. 4 is a perspective cross-sectional view of the example insert illustrated in FIG. 3.

FIGS. 3 and 4 illustrate an example insert 330 according to aspects of the invention. FIG. 3 is a perspective view of insert 330. FIG. 4 is a perspective cross-sectional view of insert 330.

Insert 330 may be adapted to fit cap 100 or a similar cap in a similar fashion to insert 130 (FIGS. 1 and 2) and includes an insert body 300, filter 360, and retainer 380. When insert 330 is fitted to cap 100, insert body 300, filter 360, and retainer 380 are retained within cap 100.

Insert body 300 includes channels 310 and 320. Retainer 380 is adapted to align with insert body 300 and includes channels 315 and 325. Optionally, retainer 380 may feature a projection 390 which may include a hole 395. When retainer 380 is aligned with insert body 300, channel 310 aligns with channel 315, and channel 320 aligns with channel 325.

Filter 360 is disposed between, and may be held in place by insert body 300 and retainer 380. Filter 360 is of a shape and size such that it occludes both the passage formed by the alignment of channel 310 and 315 and the passage formed by the alignment of channel 320 and 325.

Insert body 300 and retainer 380 may each optionally have more than two pairs of aligning holes, or may optionally have only one pair of aligning holes (not shown). In any case, filter 360 will be configured such that it occludes the resulting passages (not shown).

When insert 330 as described herein is fitted to cap 100, insert body 300, filter 360, and retainer 380 are held in place together and in alignment. Insert body 300 and/or retainer 380 may comprise a slot 394, toothed engagement 396, and/or other suitable structure may engage with cap 100 or other similar cap so as to hold insert body 300, filter 360, and retainer 380 in an alignment such that channel 310 is held in alignment with channel 315, and channel 320 is held in alignment with channel 325, and such that filter 360 occludes both the passage formed by the alignment of channel 310 and 315 and the passage formed by the alignment of channel 320 and 325. In this alignment, typical liquids are blocked by the filter and cannot pass through the passages, and typical gasses can only pass through the passages by passing through filter 360.

Retainer 380 may optionally fit insert 330 using a press fitting, screw fitting, or other suitable fitting known in the art using additional structure (not shown) such that insert body 300, filter 360, and retainer 380 are held in place together and in alignment independently of cap 100 and without requiring slot 394, toothed engagement 396, or other structures engaging with cap 100.

Figure 5:
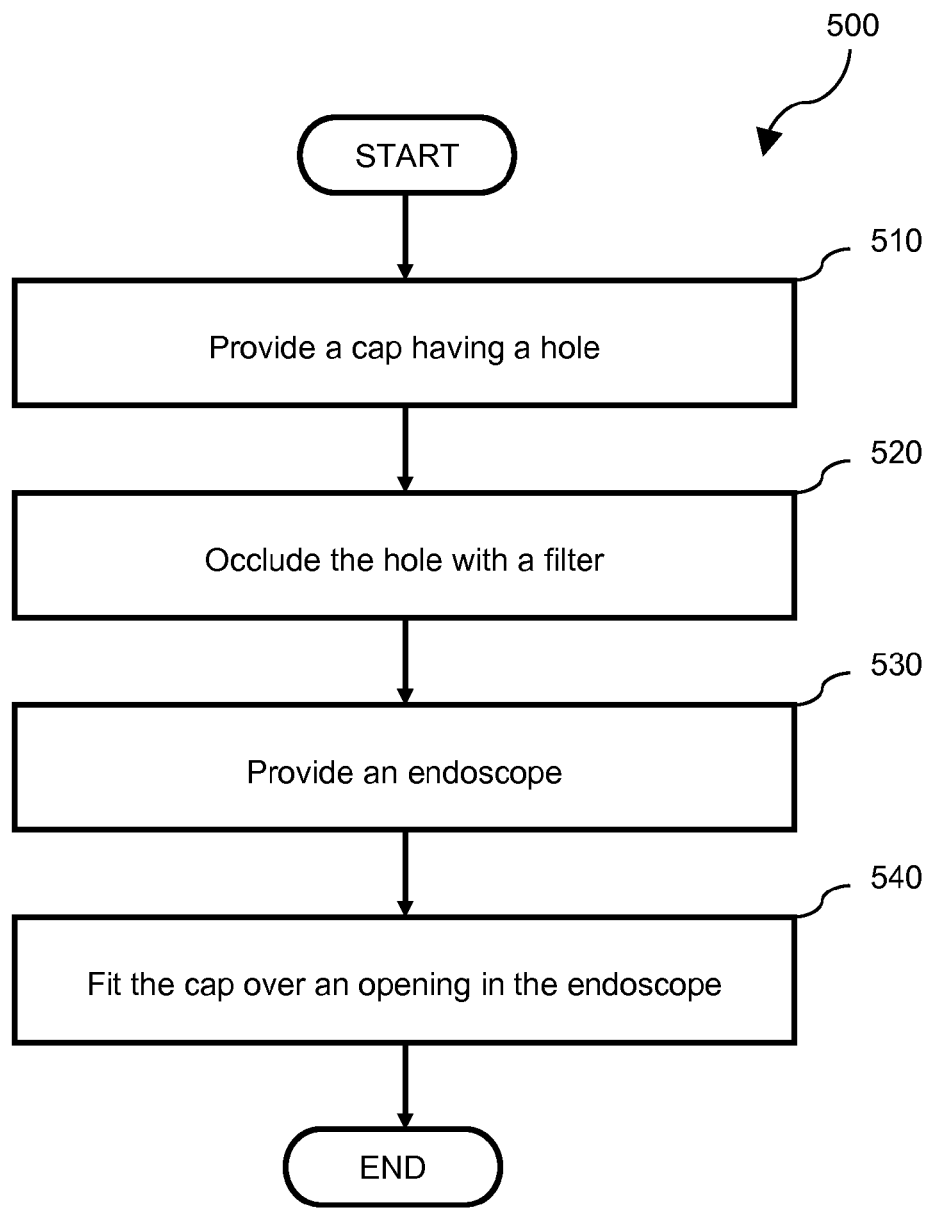
FIG. 5 is a flowchart illustrating a method according to aspects of the invention.

FIG. 5 illustrates a method 500 for equalizing pressure in an endoscope while excluding a liquid from an interior of the endoscope by providing a cap having a hole 510, occluding the hole with a filter made from a material which permits gasses to pass through the filter while preventing, substantially preventing, or substantially impeding typical liquids from passing through the filter at typical temperatures and pressures 520, Providing an endoscope 530, and fitting the cap over an opening in the endoscope 540. Those having skill in the art will appreciate that the order of these steps may be changed without departing from the invention. Optionally, the method comprises other steps (not shown) for achieving any of the implementations described with respect to FIGS. 1-4, including providing particular materials and structures described therein as would be understood by one having skill in the art.

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for equalizing pressure in an endoscope having an opening, the system comprising:
   a cap having a body configured to fit into the opening in the endoscope, the body comprising a channel extending along a longitudinal axis of the body;
   a filter occluding the channel in the body, the filter made from a material which is permeable by a gas and impermeable by a liquid; and
   a stem centrally located and extending axially within the body of the cap and along the longitudinal axis of the body, the stem configured to actuate a valve at the opening of the endoscope through contact between the stem and the valve along the longitudinal axis of the body when the cap is fitted to the opening of the endoscope,
   wherein the filter is located on the proximal end of the stem.

2. The system of claim 1, wherein the cap inhibits flow of the liquid into the endoscope by blocking the opening at the distal tip of the endoscope.

3. The system of claim 1, wherein the filter comprises a material having a surface energy lower than a surface energy of the liquid.

4. The system of claim 1, wherein the filter comprises a porous material having a pore size which permits the gas to pass through the cap while preventing the liquid from passing through the cap.

5. The system of claim 1, wherein the filter comprises porous PTFE.

6. The system of claim 1, wherein the liquid comprises water, a sterilization fluid, and at least one substance selected from the group consisting of sodium hypochlorite, glutaraldehyde; formaldehyde; ortho-phthalaldehyde; hydrogen peroxide; and peracetic acid, and combinations thereof.

7. The system of claim 1, wherein the gas comprises air.

8. The system of claim 1, wherein the gas comprises at least one substance selected from the group consisting of ethylene oxide; ozone; hydrogen peroxide; and chlorine.

9. The system of claim 1, wherein the cap fitted over the opening provides for the endoscope to be liquid-tight upon other openings in the endoscope being sealed.

10. The system of claim 1, wherein the cap comprises a seat and the filter is disposed within the seat.

11. The system of claim 1, wherein the channel is divided into sub-channels.

12. The system of claim 1, further comprising a retaining element disposed within the cap and configured to retain the filter in a position which occludes the channel.

13. The system of claim 12, wherein the retaining element includes a flange-like projection, the flange-like projection configured to retain the filter.

14. The system of claim 12, wherein when retaining element is configured as a retaining ring which is press-fit within the channel.

15. The system of claim 1, further comprising two or more sub-channels in communication with the channel and arranged within the body, the filter being located between the channel and the two or more sub-channels and configured to restrict the flow of a liquid between the channel and the two or more sub-channels, while allowing gas to flow between the channel and the two or more sub-channels.

16. The system of claim 15, wherein the stem is positioned so that it does not obstruct the sub-channels.

17. The system of claim 15, wherein the filter occludes the sub-channels.

18. The system of claim 1, wherein when the cap is fitted over the opening, the liquid cannot enter the endoscope through the opening.

19. The system of claim 1, further comprising an insert fitted into the body of the cap.

20. The system of claim 19, wherein the insert is attached using screw fitting or press fitting to the body of the cap.

21. The system of claim 19, wherein the connection between body of the cap and the insert is liquid-tight.

22. The system of claim 19, wherein the stem is incorporated into the insert.

23. The system of claim 1, wherein the body of the cap includes a bayonet style connector to connect to the opening at the distal end of the endoscope.

24. A method of equalizing pressure in an endoscope having an opening while excluding a liquid from an interior of the endoscope, the method comprising the steps of:
providing a cap having a body with a channel extending along a longitudinal axis of the body, and a stem centrally located and extending axially within the body and configured to actuate a valve at the opening of the endoscope through contact between the stem and the valve along the longitudinal axis of the body when the cap is fitted to the opening of the endoscope;
occluding the hole with a filter made from a material which is permeable by gasses and impermeable by liquids, the filter located on the proximal end of the stem;
fitting the body of the cap over the opening in the endoscope; and
actuating the valve of the endoscope with the stem.

25. A system for equalizing pressure in an endoscope having an opening at its distal end, the system comprising:
an endoscope having an opening;
a cap having a body configured to fit into the opening end of the endoscope, the body comprising a channel extending along a longitudinal axis of the body;
a filter occluding the channel in the body, the filter made from a material which is permeable by a gas and impermeable by the liquid; and
a stem extending axially within the body of the cap, the stem configured to actuate a valve at the opening of the endoscope through contact between the stem and the valve when the cap is fitted to the opening of the endoscope,
wherein the filter is located on the proximal end of the stem.

26. The system of claim 25, further comprising two or more sub-channels in communication with the channel and arranged within the body, the filter being located between the channel and the two or more sub-channels and configured to restrict the flow of a liquid between the channels.

* * * * *